(12) United States Patent
Kleinman

(10) Patent No.: US 6,555,538 B2
(45) Date of Patent: Apr. 29, 2003

(54) 5-ARYLSULFONYL-IMIDAZO[1',2':1,6] PYRIDO[2,3-B]PYRAZINE-6-AMINES AND RELATED COMPOUNDS

(75) Inventor: Edward F. Kleinman, Pawcatuck, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/095,218

(22) Filed: Mar. 11, 2002

(65) Prior Publication Data

US 2002/0147340 A1 Oct. 10, 2002

Related U.S. Application Data

(63) Continuation of application No. 09/918,099, filed on Jul. 30, 2001, now abandoned, which is a continuation of application No. 09/489,689, filed on Jan. 24, 2000, now abandoned.
(60) Provisional application No. 60/117,875, filed on Jan. 29, 1999.

(51) Int. Cl.$^7$ ................... A61K 31/4985; C07D 487/14
(52) U.S. Cl. ................ 514/250; 544/343; 544/346
(58) Field of Search ................. 544/343, 346; 514/250

(56) References Cited

PUBLICATIONS

Litvinenko et al. Chemical Abstracts, vol. 119, No. 8774 (1993).*

* cited by examiner

Primary Examiner—Emily Bernhardt
(74) Attorney, Agent, or Firm—Peter C. Richardson; Gregg C. Benson; Robert T. Ronau

(57) ABSTRACT

This application is directed to a compound of Formula I

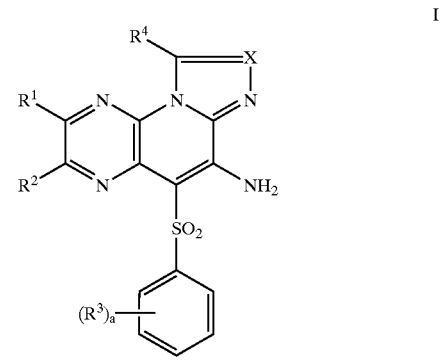

wherein a, X, $R^1$, $R^2$, $R^3$ and $R^4$ are as defined herein, useful in the treatment of respiratory, allergic, rheumatoid, body weight regulation, inflammatory and central nervous system disorders such as asthma, chronic obstructive pulmonary disease, adult respiratory diseases syndrome, shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia and AIDS.

10 Claims, No Drawings

5-ARYLSULFONYL-IMIDAZO[1',2':1,6] PYRIDO[2,3-B]PYRAZINE-6-AMINES AND RELATED COMPOUNDS

CROSS-REFERENCE TO RELATED APPLICATION

This application is a continuation of U.S. patent application Ser. No. 09/918,099, filed Jul. 30, 2001 now abandoned, which is a continuation of U.S. patent application Ser. No. 09/489,689, filed Jan. 24, 2000, now abandoned which claims the benefit of U.S. provisional patent application No. 60/117,875, filed Jan. 29, 1999.

BACKGROUND OF THE INVENTION

This invention relates to 5-arylsulfonyl-imidazo[1',2':1,6] pyrido[2,3-b]pyrazine-6-amines and related compounds. The compounds are selective inhibitors of phosphodiesterase type 4 (PDE4) and the production of tumor necrosins factor (TNF), and as such are useful in the treatment of respiratory, allergic, rheumatoid, body weight regulation, inflammatory and central nervous system disorders such as asthma, chronic obstructive pulmonary disease, adult respiratory diseases syndrome, shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia, and AIDS.

This invention also relates to a method of using such compounds in the treatment of the foregoing diseases in mammals, especially humans, and to pharmaceutical compositions containing such compounds.

Since the recognition that cyclic adenosine tri-phosphate (cAMP) is an intracellular second messenger, inhibition of the phosphodiesterases has been a target for modulation and, accordingly, therapeutic intervention in a range of disease processes. More recently, distinct classes of PDE have been recognized and their selective inhibition has led to improved drug therapy. More particularly, it has been recognized that inhibition of PDE4 can lead to inhibition of inflammatory mediator release and airway smooth muscle relaxation. Thus, compounds that inhibit PDE4, but which have poor activity against other PDE types, would inhibit the release of inflammatory mediators and relax airway smooth muscle without causing cardiovascular effects or antiplatelet effects.

Recent molecular cloning has revealed a complexity and diversity of PDE4 enzymes. It is now known that there are four distinct PDE4 isozymes (A, B, C and D), each encoded for by a separate gene. Kinetic studies of human recombinant materials suggest that these four isozymes may differ in their Km's and Vmax's for hydrolysis of cAMP. Analysis of tissue distribution of PDE4 mRNAs suggests that each isozyme may be localized in a cell-specific pattern.

SUMMARY OF THE INVENTION

The present invention relates to a compound of the formula

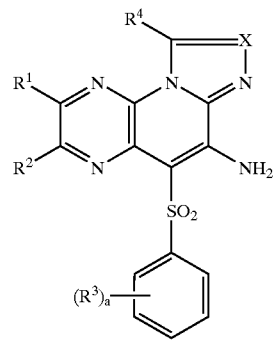

and the pharmaceutically acceptable salts thereof; wherein
a is 1, 2, 3 or 4;
X is CH or N;
$R^1$ and $R^2$ are each independently selected from hydrogen, $(C_1-C_6)$alkyl, cyano, amino, $(C_1-C_6)$alkylamino, $((C_1-C_6)$alkyl$)_2$amino, $(C_3-C_7)$cycloalkyl, $(C_6-C_{10})$aryl and a saturated or unsaturated, cyclic or bicyclic $(C_2-C_9)$heterocyclic group containing as the heteroatom one to four of the group consisting of oxygen, sulfur, nitrogen or $NR^6$ wherein $R^6$ is hydrogen or $(C_1-C_6)$alkyl;
$R^3$ and $R^4$ are each independently selected from hydrogen, halo, $(C_1-C_6)$alkyl, $(C_1-C_6)$alkoxy, cyano, hydroxy, amino, $(C_1-C_6)$alkylamino, $((C_1-C_6)$alkyl$)_2$ amino, $(C_3-C_7)$cycloalkyl, $(C_3-C_7)$cycloalkoxy, $(C_6-C_{10})$aryl or a saturated or unsaturated, cyclic or bicyclic $(C_2-C_9)$heterocyclic group containing as the heteroatom one to four of the group consisting of oxygen, sulfur, nitrogen or $NR^6$ wherein $R^6$ is defined as above;
or $R^1$ and $R^2$ may be taken together with the carbons to which they are attached to form a compound of formula II

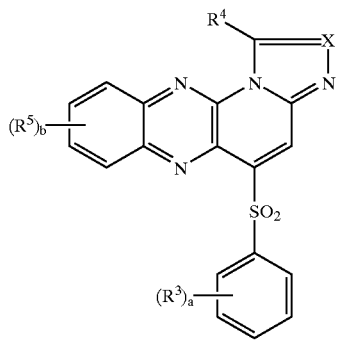

wherein
a, X, $R^3$ and $R^4$ are as defined above;
b is 1,2,3 or 4; and
$R^5$ is hydrogen, halo, $(C_1-C_6)$alkyl, $(C_1-C_6)$alkoxy, cyano, hydroxy, amino, $(C_1-C_6)$alkylamino, $((C_1-C_6)$alkyl$)_2$amino, $(C_3-C_7)$cycloalkyl, $(C_3-C_7)$cycloalkoxy, $(C_6-C_{10})$aryl or a saturated or unsaturated, cyclic or bicyclic $(C_2-C_9)$heterocyclic group containing as the heteroatom one to four of the group consisting of oxygen, sulfur, nitrogen or $NR^6$ wherein $R^6$ is defined as above.

The term "alkyl", as used herein, unless otherwise indicated, includes saturated monovalent hydrocarbon radicals having straight, branched or cyclic moieties or combinations thereof.

The term "a saturated or unsaturated, cyclic or bicyclic ($C_2$–$C_9$) heterocyclic group containing as the heteroatom one to four of the group consisting of oxygen, sulfur, nitrogen or $NR^6$ wherein $R^6$ is as defined above", as used herein, unless otherwise indicated, includes but is not limited to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl.

The term "halo", as defined herein, includes fluoro, chloro, bromo or iodo.

Preferred compounds of formula I include those wherein X is nitrogen.

Other preferred compounds of formula I include those wherein $R^1$ is hydrogen, ($C_1$–$C_6$)alkyl, amino, cycloalkyl or ($C_6$–$C_{10}$)aryl.

Other preferred compounds of formula I include those wherein $R^2$ is hydrogen, ($C_1$–$C_6$)alkyl, amino, cycloalkyl or ($C_6$–$C_{10}$)aryl.

Other preferred compounds of formula I include those wherein $R^3$ is hydrogen, halo, ($C_1$–$C_6$)alkyl, ($C_1$–$C_6$)alkoxy, cyano, amino, hydroxy, cycloalkyl or ($C_6$–$C_{10}$)aryl.

Other preferred compounds of formula I include those wherein $R^4$ is hydrogen, ($C_1$–$C_6$)alkyl, ($C_1$–$C_6$)alkoxy, amino, hydroxy, cycloalkyl or ($C_6$–$C_{10}$)aryl.

Other preferred compounds of formula II include those wherein $R^5$ is hydrogen, halo, ($C_1$–$C_6$)alkyl, ($C_1$–$C_6$)alkoxy, cyano, amino, hydroxy, cycloalkyl or ($C_6$–$C_{10}$)aryl.

More preferred compounds of formula I include those wherein X is nitrogen; $R^1$ is hydrogen, ($C_1$–$C_6$)alkyl, amino, cycloalkyl or ($C_6$–$C_{10}$)aryl; $R^2$ is hydrogen, (C–$C_6$)alkyl, amino, cycloalkyl or ($C_6$–$C_{10}$)aryl; $R^3$ is hydrogen, halo, ($C_1$–$C_6$)alkyl, cyano, amino, hydroxy, cycloalkyl or ($C_6$–$C_{10}$)aryl; and $R^4$ is hydrogen, ($C_1$–$C_6$)alkyl, amino, hydroxy, cycloalkyl or ($C_6$–$C_{10}$)aryl.

More preferred compounds of formula II include those wherein X is nitrogen; $R^3$ is hydrogen, halo, ($C_1$–$C_6$)alkyl, cyano, amino, hydroxy, cycloalkyl or ($C_6$–$C_{10}$)aryl; $R^4$ is hydrogen, ($C_1$–$C_6$)alkyl, amino, hydroxy, cycloalkyl or ($C_6$–$C_{10}$)aryl and $R^5$ is hydrogen, ($C_1$–$C_6$)alkyl, cyano, amino, hydroxy, cycloalkyl or ($C_6$–$C_{10}$)aryl.

Specific preferred compounds of formula I include the following:

5-[(4-methylphenyl)sulfonyl]-imidazo[1',2':1,6]pyrido[2,3-b]pyrazin-6-amine;

5-[(4-methylphenyl)sulfonyl]-[1,2,4]triazolo[4',3':1,6]pyrido[2,3-b]pyrazin-6-amine;

5-[(4-ethylphenyl)sulfonyl]-imidazo[1',2':1,6]pyrido[2,3-b]pyrazin-6-amine;

5-[(4-isopropylphenyl)sulfonyl]-imidazo[1',2':1,6]pyrido[2,3-b]pyrazin-6-amine;

5-[(4-propylphenyl)sulfonyl]-imidazo[1',2':1,6]pyrido[2,3-b]pyrazin-6-amine;

5-[(4-methoxyphenyl)sulfonyl]-imidazo[1',2':1,6]pyrido[2,3-b]pyrazin-6-amine;

5-[(4-ethylphenyl)sulfonyl]-[1,2,4]triazolo[4',3':1,6]pyrido[2,3-b]quinoxaline-4-amino;

5-[(4-fluorophenyl)sulfonyl]-imidazo[1',2':1,6]pyrido[2,3-b]pyrazin-6-amine;

5-[(4-chlorophenyl)sulfonyl]-imidazo[1',2':1,6]pyrido[2,3-b]pyrazin-6-amine;

5-[(3-methoxyphenyl)sulfonyl]-imidazo[1',2':1,6]pyrido[2,3-b]pyrazin-6-amine;

5-[(4-methoxyphenyl)sulfonyl]-[1,2,4]triazolo[4',3':1,6]pyrido[2,3-b]pyrazin-6-amine; and 5-[(4-methoxyphenyl)sulfonyl]-[1,2,4]triazolo[4',3':1,6]pyrido[2,3-b]quinoxaline-4-amine;

The present invention also relates to a pharmaceutical composition for the treatment of respiratory, allergic, rheumatoid, body weight regulation, inflammatory and central nervous system disorders such as asthma, chronic obstructive pulmonary disease, adult respiratory diseases syndrome, shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia and AIDS in a mammal, including a human, comprising an amount of a compound of the formula I or a pharmaceutically acceptable salt thereof, effective in such treatment and a pharmaceutically acceptable carrier.

The present invention also relates to a method for the treatment of respiratory, allergic, rheumatoid, body weight regulation, inflammatory and central nervous system disorders such as asthma, chronic obstructive pulmonary disease, adult respiratory diseases syndrome, shock, fibrosis, pulmonary hypersensitivity, allergic rhinitis, atopic dermatitis, psoriasis, weight control, rheumatoid arthritis, cachexia, Crohn's disease, ulcerative colitis, arthritic conditions and other inflammatory diseases, depression, multi-infarct dementia and AIDS in a mammal, including a human, comprising administering to said mammal an amount of a compound of the formula I or a pharmaceutically acceptable salt thereof, effective in such treatment.

DETAILED DESCRIPTION OF THE INVENTION

The following reaction Schemes illustrate the preparation of compounds of the present invention. Unless otherwise indicated a, b, X, $R^1$, $R^2$, $R^3$, $R^4$ and $R^5$ in the reaction Schemes and the discussion that follow are defined as above.

SCHEME 1

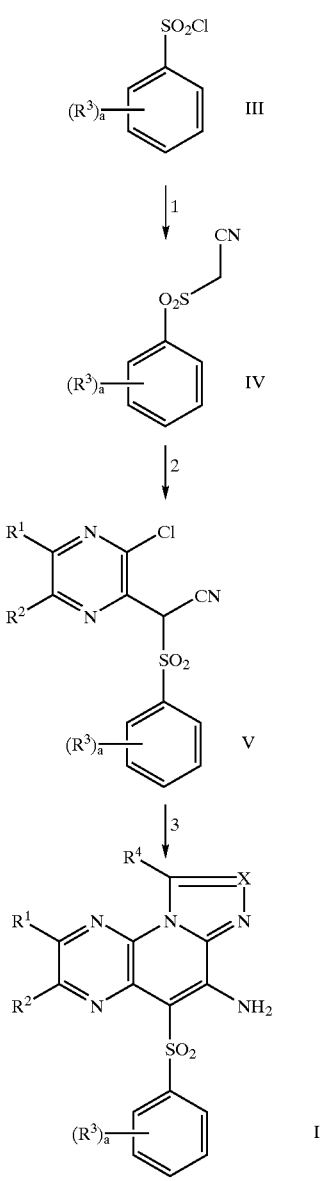

SCHEME 2

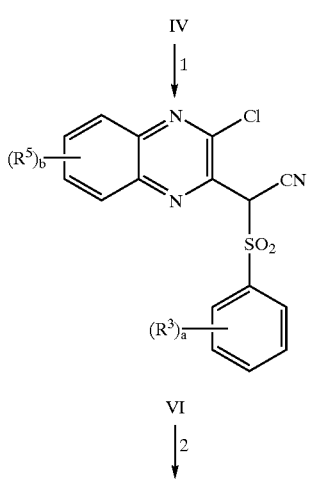

-continued

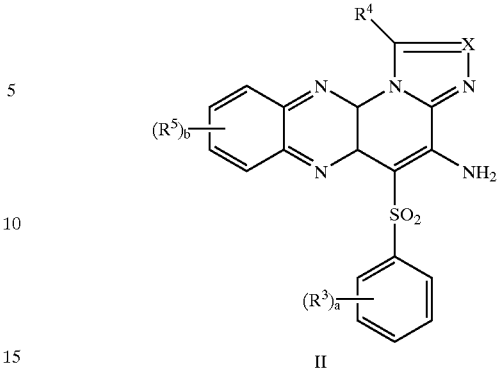

In reaction 1 of Scheme 1, the benzenesulfonyl chloride compound of formula III is converted to the corresponding cyano compound of formula IV by in situ reduction of III to the corresponding sulfinate salt followed by reaction with a haloacetonitrile, preferably bromoacetonitrile. The reaction mixture so formed is heated at a temperature between about 50° C. to about 70° C, preferably about 60° C., for a time period between about 1 hour to about 3 hours, preferably about 2 hours.

In reaction 2 of Scheme 1, the compound of formula IV is converted to the corresponding pyrazineacetonitrile compound of formula V by reacting IV with a 2,3-dichloropyrazine compound of formula

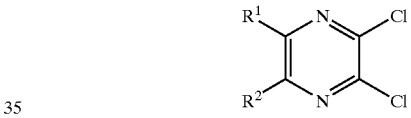

in the presence of potassium carbonate and a polar aprotic solvent, such as dimethylformamide. The reaction mixture is heated at a temperature between about 70° C. to about 90° C., preferably about 80° C., for a time period between about 6 hours to about 8 hours, preferably about 7 hours.

In reaction 3 of Scheme 1, the pyrazineacetonitrile compound of formula V is converted to the corresponding 5-arylsulfonyl-imidazo[1',2':1,6]pyrido[2,3-6]pyrazine-6-amine compound of formula I by reacting V with a 1-methylimidazole, when X is CH, or a 1-methyl-1,2,4-triazole, when X is N, in a polar aprotic solvent, such as dimethylformamide. The reaction mixture so formed is heated to a temperature of about 140° C. to about 180° C., preferably 160° C., for a time period between about 1 hour to about 8 hours, preferably about 6 hours.

In reaction 1 of Scheme 2, the compound of formula IV is converted to the corresponding benzopyrazineacetonitrile compound of formula VI by reacting IV with a dichlorobenzopyrazine compound of the formula

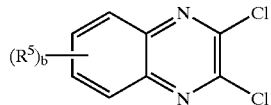

in the presence of potassium carbonate and a polar apotic solvent, such as dimethylformamide. The reaction mixture is heated at a temperature between about 70° C. to about 90° C., preferably about 80° C., for a time period between about 6 hours to about 8 hours, preferably about 7 hours.

In reaction 2 of Scheme 2, the compound of formula VI is converted to the corresponding compound of formula II according to the procedure described above in reaction 3 of Scheme 1.

The compounds of formula I that are basic in nature are capable of forming a wide variety of different salts with various inorganic and organic acids. Although such salts must be pharmaceutically acceptable for administration to humans or animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Pharmaceutically acceptable salts of amino groups include hydrochloride, hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. Cationic salts of the compounds of formula I are similarly prepared except through reaction of a carboxy group with an appropriate cationic salt reagent such as sodium, potassium, calcium, magnesium, ammonium, N,N'-dibenzyiethylenediamine, N-methylglucamine (meglumine), ethanolamine, tromethamine, or diethanolamine.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

For administration to humans in the curative or prophylactic treatment of inflammatory diseases, oral dosages of a compound of formula I or a pharmaceutically acceptable salt thereof (the active compounds) are generally in the range of 0.1 to 1000 mg daily, in single or divided doses, for an average adult patient (70 kg). The active compounds can be administered in single or divided doses. Individual tablets or capsules should generally contain from 0.1 to 100 mg of active compound, in a suitable pharmaceutically acceptable vehicle or carrier. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For human use, the active compounds of the present invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic.

Additionally, the active compounds may be administered topically when treating inflammatory conditions of the skin and this may be done by way of creams, jellies, gels, pastes, and ointments, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The ability of the compounds of formula I or the pharmaceutically acceptable salts thereof to inhibit $PDE_4$ may be determined by the following assay.

Inhibition of PDE4 Isozymes

Preparation of Test Compounds

Compounds are dissolved in dimethyl sulfoxide at a concentration of $1 \times 10^{-2}$ M, or to a desired higher concentration if solubility is an issue then diluted 1:25 in water ($4 \times 10^{-4}$ M compound, 4% DMSO). Further serial dilutions are made in 4% dimethyl sulfoxide to achieve desired concentrations. Final dimethyl sulfoxide concentration in assay is 1%.

In duplicate, the following are added in order to a scintillation vial (all concentrations are given as final concentrations in vial).

25 μl compound of dimethyl sulfoxide (1%, for blank)
25 μl [³H] cAMP-containing assay buffer (1 μM [³H] cAMP, 50 mM Tris, 10 mM MgCl₂, pH 7.5)
25 μl 5'-nucleotidase (0.001 unit) (Sigma #N5880)
25 μl PDE4 isozyme (1/1200–1/2400 dilution in Prep #1)

The reaction vials are shaken and placed in a water bath (3.7° C.) for 30 minutes, at which time the reaction is stopped by adding 1 ml Dowex 1×8 resin, chloride form (1:3 slurry in distilled water). Three ml Ready Safte scintillation fluid are added directly to each vial. Mix each vial well and count radioactivity after resin has settled (approx. 4 hours at room temperature).

Data Calculation and Interpretation

Percent inhibition is determined by the formula:

$$\% \ inh = 1 - \frac{\text{avg. cpm (test compound)} - \text{avg. cpm (blank)}}{\text{avg. cpm (control (no compound))} - \text{avg. cpm (blank)}} \times 100$$

IC50 is defined as that concentration of compound which inhibits 50% of radioactivity, and is determined by Microsoft Excel or other appropriate software.

The present invention is illustrated by the following examples, but is not limited to the details thereof.

Preparation 1

[(4-Ethylphenyl)sulfonyl]-acetonitrile

In a 125 mL, three-necked flask fiited with thermometer, addition funnel, and glass stopper was placed 11.5 grams (91.2 mmol) of sodium sulfite, 8.32 grams (97.7 mmol) of sodium bicarbonate, and 50 mL of water. After heating the mixture to 75–80° C., 10.0 grams (48.9 mmol) of 4-ethylbenzenesulfonyl chloride was added dropwise over 0.5 hours. When the addition was complete, heating was continued for 3 hours at which time a white precipitate formed. The suspension was cooled to room temperature and allowed to stir for 16 hours. The precipitate was collected by filtration, washed with cold water, combined with a second crop from the filtrate, and dried under high vaccum to give 13.9 grams (>100% yield) of crude sodium 4-ethylbenzenesulfinate.

In a small Parr bottle was placed the salt above, 3.09 mL (5.33 grams, 44.9 mmol) of bromoacetonitrile, and 0.488 grams of aliquat™-336. The contents were agitated on a Vortex-2 Genie™ for 5 minutes using a spatula to maintain homogeneity. The bottle was transferred to an oil bath and heated for 2 hours at 60° C., as the mixture softened, turned pink-orange, and then hardened. The solid was extracted with 250 mL of ethyl acetate, filtered, and evaporated to a solid. Trituration in methylene chloride gave 5.61 grams (55% yield) of the title compound as an off-white solid. Melting Point: 120–121° C. Anal. Calcd for $C_{10}H_{11}NO_2S$: C, 54.40; H, 5.30; N, 6.69. Found: C, 57.29; H, 5.39; N, 6.6.1.

Preparations 2–4

The compounds of Preparations 2–4 were prepared according to the procedure of Preparation 1 substituting the indicated sulfonyl chloride for 4-ethylbenzenesulfonyl chloride.

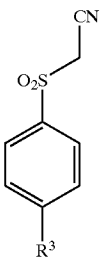

| Preparation | R³ | M.P. (° C.) | C, H, N Analysis |
|---|---|---|---|
| 2 | CH(CH₃)₂ | 64–66 | Calcd for $C_{11}H_{13}NO_2S$: C, 59.17; H, 5.87; N, 6.27. Found: C, 59.31; H, 5.82; N, 6.27. |
| 3 | n-C₃H₇ | 123–134 | Calcd for $C_{11}H_{13}NO_2S$: C, 59.17; H, 5.87; N, 6.27. Found: C, 59.42; H, 5.82; N, 6.23. |
| 4 | OCH₃ | 115–117 | Calcd for $C_9H_9NO_3S$: C, 51.12; H, 4.29; N, 6.63. Found: C, 51.27; H, 4.16; N, 6.63. |

Preparation 5

3-Chloro-□-[(4-methylphenyl)sulfonyl]2-pyrazineacetonitrile

A mixture of 6.38 grams (32.7 mmol) of (4-methylbenzenesulfonyl)acetonitrile (for preparation, see: Bram, G. et al., *Synthesis*, 1987, 56), 4.87 grams (32.7 mmol) of 2,3-dichloropyrazine, 4.97 grams (36.0 mmol) of potassium carbonate, and 10 mL of dimethylformamide was heated for 7 hours at 80° C. The solvent was removed by vaccum distillation, and the residue was diluted with 100 mL of aqueous 1 N hydrochloric acid solution and extracted with ethyl acetate (1×150 mL, 1×100 mL). The combined extracts were washed with brine (1×100 mL), dried (magnesium sulfate) and evaporated to give 8.9 grams of a dark oil. Purification by flash chromatography using a 30–50% ethyl acetate-hexane eluant gave 2.35 grams of solid which was triturated in ether to afford 2.20 grams (20% yield) of the title compound as a white solid. Melting Point: 148–151° C. (lit. 126° C. (Litvinenko, S. V. et al., *Chem. Heterocycl. Compd.* (Eng. Transl.), 1992, 28, 93)). Anal. Calcd for $C_{13}H_{10}N_3O_2ClS$: C, 50.74; H, 3.28; N, 13.65. Found: C, 50.45; H, 3.53; N, 13.77.

Preparations 6–9

The compounds of Preparations 6–9 were prepared according to the procedure of Preparation 5 substituting the indicated substrate for (4-methylbenzenesulfonyl)acetonitrile.

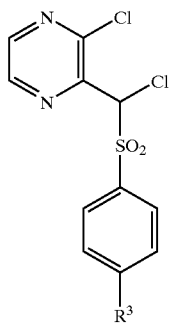

| Preparation | R³ | Substrate | M.P. (° C.) | C, H, N Analysis |
|---|---|---|---|---|
| 6 | C₂H₅ | Compound of Pep. 1 | 129–131 | Calcd for C₁₄H₁₂N₃O₂ClS: C, 52.26; H, 3.76; N, 13.06. Found: C, 52.38; H, 3.59; N, 12.97. |
| 7 | CH(CH₃)₂ | Compound of Prep. 2 | 88–94 | Calcd for C₁₅H₁₄N₃O₂ClS: C, 53.49; H, 4.49; N, 12.48. Found: C, 53.72; H, 4.21; N, 12.47. |
| 8 | n-C₃H₇ | Compound of Prep. 3 | 100–103 | Calcd for C₁₅H₁₄N₃O₂ClS: C, 53.49; H, 4.49; N, 12.48. Found: C, 53.70; H, 4.31; N, 12.34. |
| 9 | OCH₃ | Compound of Prep. 4 | 135–136 | Calcd for C₁₃H₁₀N₃O₃ClS: C, 48.23; H, 3.11; N, 12.98. Found: C, 48.42; H, 3.15; N, 12.86. |

Preparation 10

3-Chloro-□-[(4-ethylphenyl)sulfonyl]-2-quinoxalineacetonitrile le;2qThe title compound was prepared as a tan powder, melting point 208–211° C., according to the procedure of Preparation 5 substituting the compound of Preparation 1 for (4-methylbenzesulfonyl)acetonitrile and substituting 2,3-dichlorquinazoline for 2,3-dichloropyrazine. Calcd for C₁₈H₁₄N₃O₂SCI: C, 58.14 H, 3.79; N, 11.30. Found: C, 58.15; H, 3.59; N, 11.32.

EXAMPLE 1

5-[(4-Methylphenyl)sulfonyl]-imidazo[1',2':1,6]pyrido[2,3-b]pyrazin-6-amine

A mixture of 360 mg (1.17 mmol) of the compound of Preparation 5, 0.280 mL (288 mg, 3.51 mmol) of 1-methylimidiazole, and 2 mL of dimethylformamide was heated for 1.5 hours at 160° C. An additional 0.280 mL of 1-methylimidazole was added and heating was continued for 4.5 hours. The solvent and excess 1-methylimidazole was removed by distillation under high vaccum, and the dark solid residue was extracted with 150 mL of boiling toluene and filtered. The filtrate was evaporated to give 234 mg of a dark solid brown solid. The insoluble material from the hot toluene extract was extracted with 100 mL of boiling chloroform, filtered, and evaporated to give 214 mg of a dark brown solid. Both solids were purified separately by flash chromatography using 5% acetone-chloroform as eluant, and the enriched fractions from each purification were combined and evaporated to give 301 mg of a yellow solid. Trituration in ether followed by rercrystallization from toluene afforded 148 mg (37% yield) of the title compound as a fluffy yellow solid. Melting Point: 294–295° C. Anal. Calcd for C₁₆H₁₃N₅O₂S: C, 56.63; H, 3.86; N, 20.64. Found: C, 56.87; H, 3.79; N, 20.61.

EXAMPLES 2–6

The compounds of Examples 2–6 were prepared according to the procedure of Example 1 substituting the indicated substrate for the compound of Preparation 5 and, in the case of Example 2, substituting 1-methyl-1,2,4-triazole for 1-methylimidazole. In some cases, reactions were performed neat in excess 1-methylimidazole or 1-methyl-1,2,4-triazole.

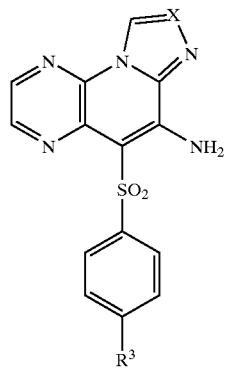

| Example | R³ | X | Substrate | M.P. (° C.) | Spectral or Analytical Data |
|---|---|---|---|---|---|
| 2 | CH₃ | N | Compound of Prep. 5 | >300° C. | Anal. Calcd for $C_{15}H_{12}N_6O_2S$: C, 52.93; H, 3.55; N, 24.69. Found: C, 53.31; H, 3.55; N, 24.68. |
| 3 | CH₂CH₃ | CH | Compound of Prep. 6 | 267.5–268.5 | Anal. Calcd for $C_{17}H_{15}N_5O_2S$: C, 57.78; H, 4.28; N, 19.82. Found: C, 57.88; H, 4.24; N, 19.77. |
| 4 | CH(CH₃)₂ | CH | Compound of Prep. 7 | 241–244 | Anal. Calcd for $C_{18}H_{17}N_5O_2S$: C, 58.84; H, 4.66; N, 19.06. Found: C, 58.63; H, 4.55; N, 18.88. |
| 5 | n-C₃H₇ | CH | Compound of Prep. 8 | 231–232 | ¹H NMR(DMSO-d⁶)d 0.84(3H, t, J=7 Hz), 1.49–1.61(2H, m), 2.58(2H, t, J=7.5Hz), 7.35(2H, d, J=8Hz), 7.74(1 H, d, J=1Hz), 7.99(2H, d, J=8Hz), 8.05(1H, br s), 8.26(1H, br s), 8.34(1 H, d, J=2.5Hz), 8.54(1H, d, J=1Hz), 8.57(1H, d, J=2.5Hz). |
| 6 | OCH₃ | CH | Compound of Prep. 9 | 269–270 | ¹H NMR(DMSO-d⁶)d 3.77(3H, s), 7.01 (2H, d, J=8Hz), 7.71–7.72(1H, m), 7.98(1H, br s), 8.00(2H, d, J=8Hz), 8.21(1H, br s), 8.32–8.33(1H, m), 8.51–8.52(1H, m), 8.555–8.563(1H, m). |

EXAMPLE 7

5-[(4-Ethylphenyl)sulfonyl]-[1,2,4]triazolo[4',3':1,6]pyrido[2,3-b]quinoxalin-4-amine The title compound was prepared as a fluffy yellow solid, melting point>300° C., according to the procedure Example 1 substituting the compound of Preparation 10 for the compound of Preparation 5 and substituting 1-methyl-1,2,4-triazole for 1-methylimidazole. Calcd for $C_{15}H_{16}N_6O_2S$: C, 59.39; H, 3.99; N, 20.78. Found: C, 59.33; H, 3.99; N, 21.10.

EXAMPLE 8

5-[(4-Hydroxyphenyl)sulfonyl]-imidazo[1',2':1,6]pyrido[2,3-b]pyrazin-6-amine

A mixture of 97 mg (0.27 mmol) of the compound of Example 6, 360 mg (2.7 mmol) of lithium iodide, and 5 mL of collidine was heated for 4 hours at 210° C. The solvent was removed by distillation under vaccum, and the residue was taken up in 100 mL of ethyl acetate, washed with saturated aqueous sodium sulfate solution (1×25 mL), aqueous 1 N hydrochloric acid solution (1×100 mL), water (1×100 mL), saturated aqueous sodium sulfate solution (1×50 mL), and brine (1×50 mL). Solids were removed by filtration, and the filtrate was dried (magnesium sulfate) and evaporated to give 110 mg of a solid which was triturated in hot methanol to afford 90 mg (95% yield) of the title compound as a bright yellow solid. Melting Point: >300° C. AMPI MS (m/e) 341 (M⁺).

What is claimed is:

1. A compound of the formula

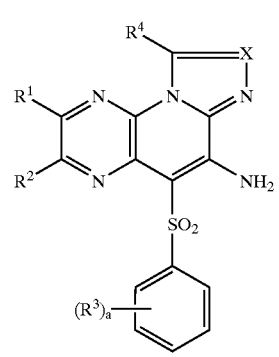

I or a pharmaceutically acceptable salt thereof; wherein
a is 1, 2, 3 or 4;
X is N;
R¹ and R² are each independently selected from hydrogen, ($C_1$–$C_6$)alkyl, cyano, amino, ($C_1$–$C_6$)alkylamino, (($C_1$–$C_6$)alkyl)₂amino, ($C_3$–$C_7$)cycloalkyl, ($C_6$–$C_{10}$)aryl;
R³ and R⁴ are each independently selected from hydrogen, halo, ($C_1$–$C_6$)alkyl, ($C_1$–$C_6$)alkoxy, cyano, hydroxy, amino, $(C_1-C_6)$alkylamino, $((C_1-C_6)$alkyl$)_2$ amino, $(C_3-C_7)$cycloalkyl, $(C_3-C_7)$cycloalkoxy, $(C_6-C_{10})$aryl;

or $R^1$ and $R^2$ may be taken together with the carbons to which they are attached to form a compound of formula II

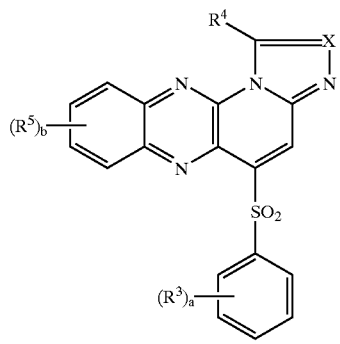

wherein a, X, $R^3$ and $R^4$ are as defined above;

X is CH or N;

b is 1, 2, 3 or 4; and $R^5$ is hydrogen, halo, $(C_1-C_6)$alkyl, $(C_1-C_6)$alkoxy, cyano, hydroxy, amino, $(C_1-C_6)$alkylamino, $((C_1-C_6)$alkyl$)_2$amino, $(C_3-C_7)$cycloalkyl, $(C_3-C_7)$cycloalkoxy, $(C_6-C_{10})$aryl.

2. A compound according to claim 1, wherein $R^1$ is hydrogen, $(C_1-C_6)$alkyl, amino, cycloalkyl or $(C_6-C_{10})$aryl.

3. A compound according to claim 1, wherein $R^2$ is hydrogen, $(C_1-C_6)$alkyl, amino, cycloalkyl or $(C_6-C_{10})$aryl.

4. A compound according to claim 1, wherein $R^3$ is hydrogen, halo, $(C_1-C_6)$alkyl, $(C_1-C_6)$alkoxy, cyano, amino, hydroxy, cycloalkyl or $(C_6-C_{10})$aryl.

5. A compound according to claim 1, wherein $R^4$ is hydrogen, $(C_1-C_6)$alkyl, $(C_1-C_6)$alkoxy, amino, hydroxy, cycloalkyl or $(C_6-C_{10})$aryl.

6. A compound according to claim 1, wherein $R^5$ is hydrogen, $(C_1-C_6)$alkyl, $(C_1-C_6)$alkoxy, cyano, amino, hydroxy, cycloalkyl or $(C_6-C_{10})$aryl.

7. A compound according to claim 1, wherein X is nitrogen; $R^1$ is hydrogen, $(C_1-C_6)$alkyl, amino, cycloalkyl or $(C_6-C_{10})$aryl; $R^2$ is hydrogen, $(C_1-C_6)$alkyl, amino, cycloalkyl or $(C_6-C_{10})$aryl; $R^3$ is hydrogen, halo, $(C_1-C_6)$alkyl, cyano, amino, hydroxy, cycloalkyl or $(C_6-C_{10})$aryl; and $R^4$ is hydogen, $(C_1-C_6)$alkyl, amino, hydroxy, cycloalkyl or $(C_6-C_{10})$aryl.

8. A compound according to claim 1, wherein X is nitrogen; $R^3$ is hydrogen, halo, $(C_1-C6)$alkyl, cyano, amino, hydroxy, cycloalkyl or $(C_6-C_{10})$aryl; $R^4$ is hydrogen, $(C_1-C_6)$alkyl, $(C_1-C_6)$alkoxy, amino, hydroxy, cycloalkyl or $(C_6-C_{10})$aryl and $R^5$ is hydrogen, $(C_1-C_6)$alkyl, cyano, amino, hydroxy, cycloalkyl or $(C_6-C_{10})$aryl.

9. A compound of claim 1, wherein said compound is:
5-[(4-methylphenyl)sulfonyl]-[1,2,4]triazolo[4',3':1,6] pyrido[2,3-b]pyrazin-6-amine;
5-[(4-ethylphenyl)sulfonyl]-[1,2,4]triazolo[4',3':1,6]pyrido [2,3-b]quinoxaline-4-amine;
5-[(4-methoxyphenyl)sulfonyl]-[1,2,4]triazolo[4',3':1,6] pyrido[2,3-b]pyrazin-6-amine; and
5-[(4-methoxyphenyl)sulfonyl]-[1,2,4]triazolo[4',3':1,6] pyrido[2,3-b]quinoxaline-4-amine.

10. A pharmaceutical composition comprising an effective amount of a compound of claim 1 or a pharmaceutically acceptable salt thereof and a pharmaceutically acceptable carrier.

* * * * *